United States Patent [19]

Toma

[11] Patent Number: 5,697,937
[45] Date of Patent: Dec. 16, 1997

[54] SURGICAL CLAMP WITH MANIPULABLE GUIDE MEANS

[76] Inventor: Doina Toma, 2 Weybridge Rd., Great Neck, N.Y. 11023

[21] Appl. No.: 606,334

[22] Filed: Feb. 23, 1996

[51] Int. Cl.⁶ .................................................. A61B 17/42
[52] U.S. Cl. ........................ 606/119; 606/172; 606/205
[58] Field of Search .............................. 606/119, 120, 606/121, 122, 125, 126, 157, 172, 205, 206, 207, 174

[56] References Cited

U.S. PATENT DOCUMENTS

| | | | |
|---|---|---|---|
| 3,035,582 | 5/1962 | Seiger | 606/119 |
| 4,819,636 | 4/1989 | Gerich et al. | 606/157 |
| 5,562,680 | 10/1996 | Hasson | 606/119 |

*Primary Examiner*—Michael Buiz
*Assistant Examiner*—Kevin Truong
*Attorney, Agent, or Firm*—Ladas & Parry

[57] ABSTRACT

A surgical instrument for fixation and elevation of an internal body of a female patient which instrutment comprises first and second pivotably connected arms having ends which can be moved towards and away from one another when the arms are pivotably moved, clamp on the ends of the arms for engaging the internal body part of the patient to manipulate and elevate the body part, and a projecting guide member fixed on one of said arms and including a manually engagable portion remote from the arms for manipulating said arms remotely therefrom to manipulate and elevate said body part. The surgical instrument can be provided with a cylindrical attachment for the mobilization/manipulation of the vagina in patients lacking a uterus. The surgical instrument can also be provided with a catheter guiding hook for guiding a catheter to the bladder of the patient.

16 Claims, 6 Drawing Sheets

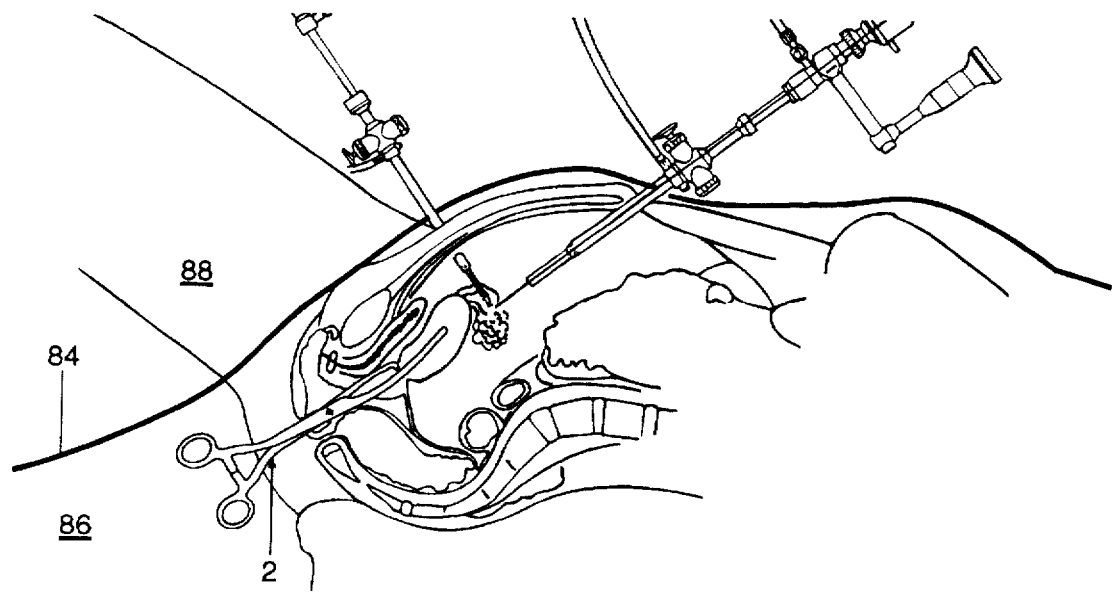
FIG. 7 ( a )
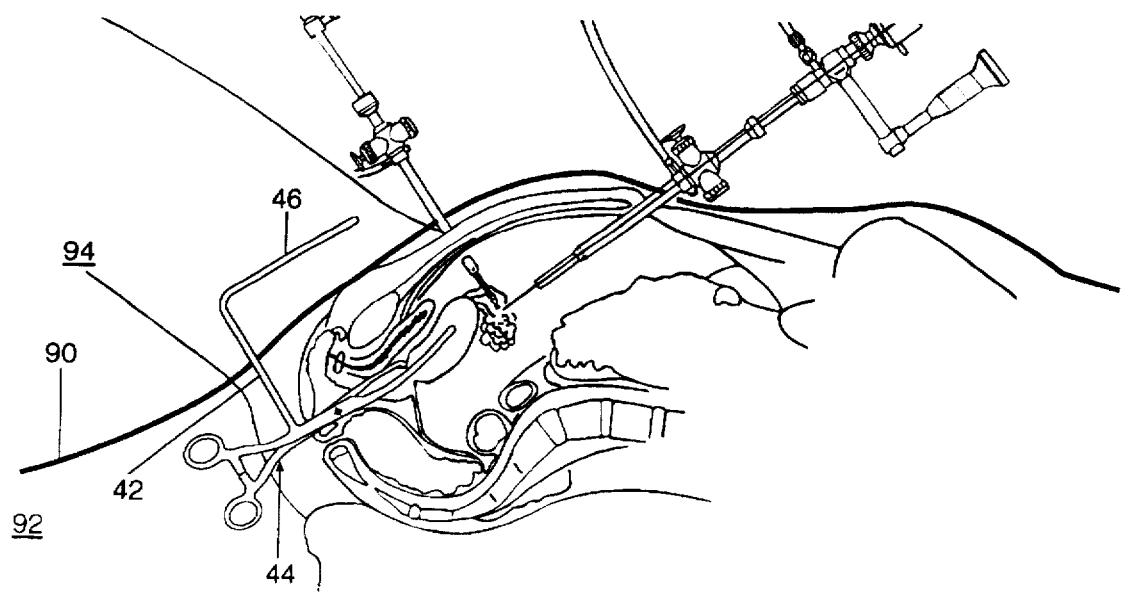
FIG. 7 ( b )

5,697,937

SURGICAL CLAMP WITH MANIPULABLE GUIDE MEANS

BACKGROUND OF THE INVENTION

1. Field of Invention

This invention relates to a surgical clamp, and more particularly to a surgical clamp which can be easily manipulated to move the uterus of a patient or, if the uterus has been removed, to move the vagina and bladder of the patient.

2. Description of the Related Art

For laparoscopic and other abdominal operations where the immobilization of an organ, such as the uterus, is desired, surgeons currently use a uterine clamp having two pivotably connected arms of unequal length. Such a clamp is depicted in FIG. 1. As shown in FIG. 1, the clamp 2 has a long arm 4 with a clamping end 6 that may be introduced into a uterus 18, and a short arm 8 with a clamping end 10 that attaches to the cervix of the uterus 18. The respective arms 4 and 8 pivot around pivot 12 and can be moved towards and away from each other by manipulation of finger-engaging portions 14 and 16 of the clamp. The finger-engaging portions 14 and 16 are disposed on an opposite end of clamp 2 from clamping ends 6 and 10. Clamp 2 is shown in FIG. 1 in closed position with the clamping ends engaging the uterus 18. The clamp may be locked in the clamping position by a locking member 20 which holds the finger-engaging portions 14 and 16 together. It can readily be appreciated that, with the clamp in a clamped position, the uterus 18 can be moved by manipulating the clamp at finger-engaging portions 14 and 16.

In use, the prior art clamp has several disadvantages. The end of the clamp affixed to the uterus is positioned in an operating area 22 that must be kept free from pathogens. By virtue of the substantially rectilinear configuration of clamp 2, the finger-engaging portions 14 and 16 of the clamp should also be positioned in the sterile operating area 22 during most manipulations of the uterus 18. It can readily be appreciated that, in the fixation/elevation of the uterus 18 during surgery using the prior art clamp, it is necessary for a nurse or other person assisting a surgeon with the manipulation of the uterus to maintain a presence in the sterile operating area 22.

Another drawback of the prior art clamp is that manipulation of the finger-engaging portions 14 and 16 of the clamp requires the nurse or other assistant to be positioned facing the uterus such that the assistant's directional orientation is reversed from that of the patient being treated (i.e., the assistant's "right" is the patient's "left" and vice versa). This positioning can be inconvenient and, moreover, can cause confusion in communications between the surgeon and the assistant. For example, when the surgeon directs movement toward the left side of the patient, the assistant must remember that this is toward the right in the assistant's reverse or mirror orientation. Additionally, the surgeon and the assistant must face in the same direction next to one another, causing interference in a limited space.

An additional drawback of the prior art clamp is that the clamp is not adapted for use in cases where the patient has had her uterus removed and manipulation/elevation of the vagina and bladder is necessary. What has been needed is a more versatile clamp that avoids the drawbacks of the prior art clamp.

SUMMARY OF THE INVENTION

It is an object of the invention to provide an improved surgical clamp which makes possible the mobilization and manipulation of the uterus of a patient from an aseptic area that is not within the sterile operating area.

It is another object of the invention to provide an instrument which is adaptable for use in those cases where the patient has had a hysterectomy.

A further object of the invention is to provide a clamp that can be manipulated from a position that places the manipulator in the same directional orientation as the patient to be treated.

In accordance with the above and other objects of the invention, there is provided a surgical instrument for fixation and elevation of an internal body of a female patient which instrument comprises first and second pivotably connected arms having ends which can be moved towards and away from one another when the arms are pivotably moved, clamp means on the ends of the arms for engaging the internal body part of the patient to manipulate and elevate the body part, and a projecting guide member fixed on one of said arms and including a manually engagable portion remote from the arms for manipulating said arms remotely therefrom to manipulate and elevate said body part.

In a preferred embodiment of the invention, the arms have opposite ends remote from the ends with the clamp means and finger-engaging portions are provided at the opposite ends. The guide member includes a portion extending perpendicularly from the one arm. The manually engagable portion extends from the one portion in a direction away from the finger-engaging portions.

In another embodiment of the invention the guide member is of L-shape. The arms are connected in scissor fashion, with the guide member extending from the arms in the vicinity of the pivotable connection of the arms.

In accordance with yet another embodiment, the manually engagable portion extends approximately parallel to the arms when the arms are closed and the arrangement is such that movement of the manually engagable member produces corresponding movement of the clamp means in the same direction. The body part of the female to be manipulated is the uterus, and the clamp means is shaped to engage and clamp the uterus. For patients lacking a uterus, the instrument comprises an additional element attachable to one of the arms and of cylindrical shape.

BRIEF DESCRIPTION OF THE DRAWINGS

Other features and advantages of the present invention will become more apparent in the following detailed description, including drawings, all of which show a non-limiting form of the present invention, and in which:

FIG. 7(a) shows a prior art uterine clamp in use during an operating procedure; and FIG. 7(b) shows a surgical instrument of the present invention in use during an operating procedure.

DETAILED DESCRIPTION

Figure 2:
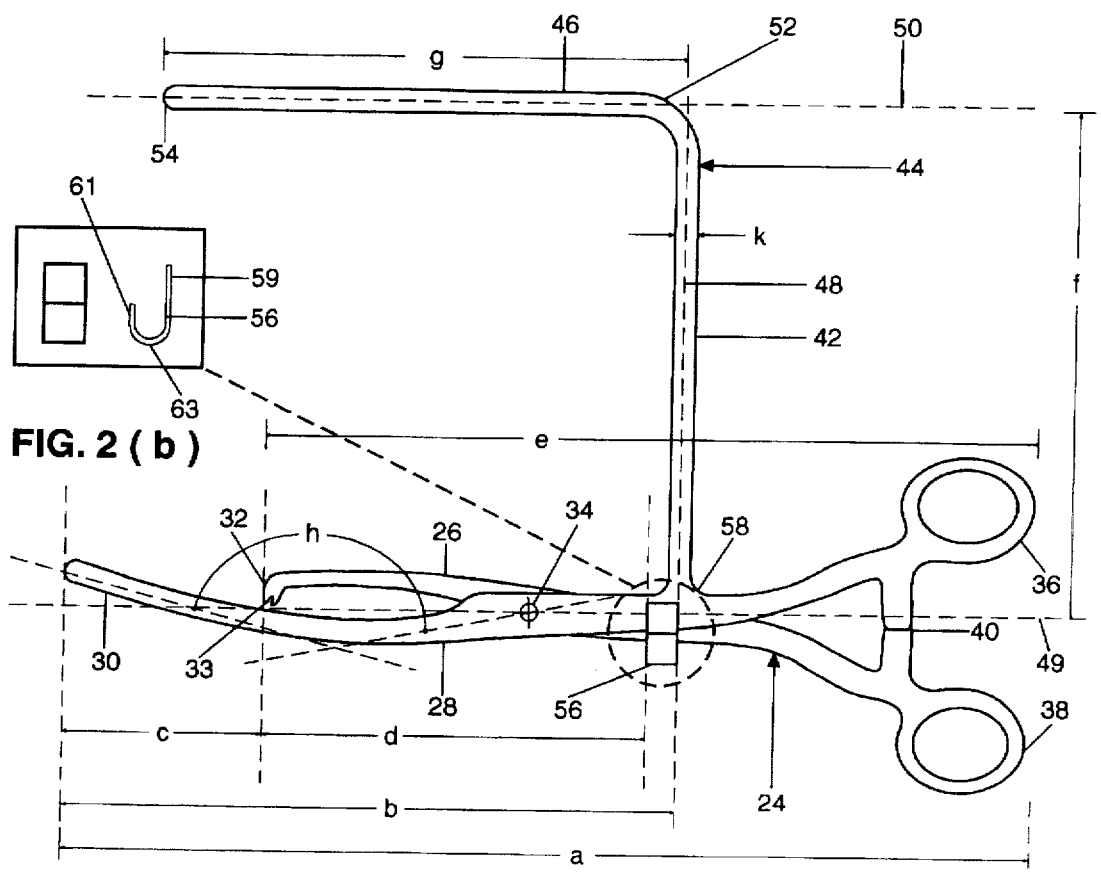
FIG. 2(a) shows a surgical instrument of the present invention.
FIG. 2(b) is a side view of a catheter guide of the surgical instrument shown in FIG. 2(a)

Referring to the Drawing, FIG. 2 shows a uterine clamp 24 in a preferred embodiment of the invention. Clamp 24 has a short arm 26 and a long arm 28 pivotably connected at pivot 34 in scissor fashion. Short arm 26 has clamping end 32 at one end and a finger-engaging portion 38 at an opposite end. Long arm 28 has clamping end 30 at one end and finger-engaging portion 36 at an opposite end. Clamp 24 is provided with a locking member 40 to maintain the clamp in a locking position. Clamping end 32 of short arm 26 is provided with a claw 33 to facilitate gripping of an outer portion of the uterus (cervix). Clamp 24 is also provided with a guiding hook 56 for holding a tube or catheter to be inserted into the bladder when the clamp is in use. FIG. 2(b) shows guiding hook 56 in a side view wherein the hook can be seen to be of "J" shape, including parallel members 59 and 61 connected by arcuate member 63.

In addition to the above features, the clamp 24 is provided with an L-shaped grip or guide member 44 that projects from an arm of the clamp 24. Grip 44 is shown projecting from long arm 28. As shown in FIG. 2(a), grip 44 is comprised of members 42 and 46, which members may be integrally formed. Member 42 has an axis 48 that is perpendicular to the axis 49 defined by arms 26 and 28. Member 46 of grip 44 has an axis that is perpendicular to axis 48 of member 42. In the embodiment depicted in FIG. 2, members 42 and 46 of grip 44 lie in substantially the same plane as arms 26 and 28 and member 46 is substantially parallel to these arms. Member 46 is shown extending from member 42 in the direction of clamping ends 30 and 32 and away from finger-engaging portions 36 and 38 of arms 26 and 28. The member 42 of grip 44 is affixed to arm 28 in the vicinity of the pivot connection of arms 26 and 30 to balance the weight of the instrument and cause the clamps to move in correspondence with the end of the member 46.

The dimensions of clamp 24 are specifically designed to facilitate its use with the uterus of a patient. So, for example, end 30 of arm 28 is of a curved configuration that can be accommodated in the uterus of a patient and thus permits insertion of arm 28 into the uterus. The respective lengths of arms 26 and 28 are such as to permit claw 33 of arm 26 to contact the narrow outer end of the uterus when end 30 of arm 28 is inserted a substantial distance into the uterus. Grip 44 is attached to arm 26 or 28 at the balance position of the instrument and sufficiently remote from ends 32 and 30 to prevent member 46 from contacting any bodily organs in use, such as the walls of the vagina (see FIG. 3). On the other hand, the attachment point for grip 44 is such as to provide a proper balance between portions of the clamp on either side of attachment point 58.

In a typical embodiment, the length of the clamp, as measured from end 30 of long arm 28 to the opposite end 38 (reference character "a" in FIG. 2(a)) is preferably about 300 mm. Grip 44 is preferably attached to clamp 24 a distance (reference character "b") from end 30 of about 180 mm. The length of short arm 26 (reference character "e") is preferably about 240 mm. The width of catheter guiding hook 56 is preferably about 10 mm whereby reference characters "c" and "d" are preferably about 60 mm and 110 mm respectively. The radius of curvature of long arm 28, as indicated at angle "h" is preferably about 160°. With respect to grip 44, the height of member 42 (reference character "f") is preferably about 260 mm. Member 46 has a length (reference character "g") of preferably about 160 mm. The width or diameter of grip 44 ("k") is preferably about 7 mm.

The dimensions of the grip 44 are related to the dimensions of the arms 26, 28 and especially the clamp means 32 so that movement of the grip 44 by the user will be followed by a corresponding 1:1 movement of the body part clamped by the instrument.

Figure 3:
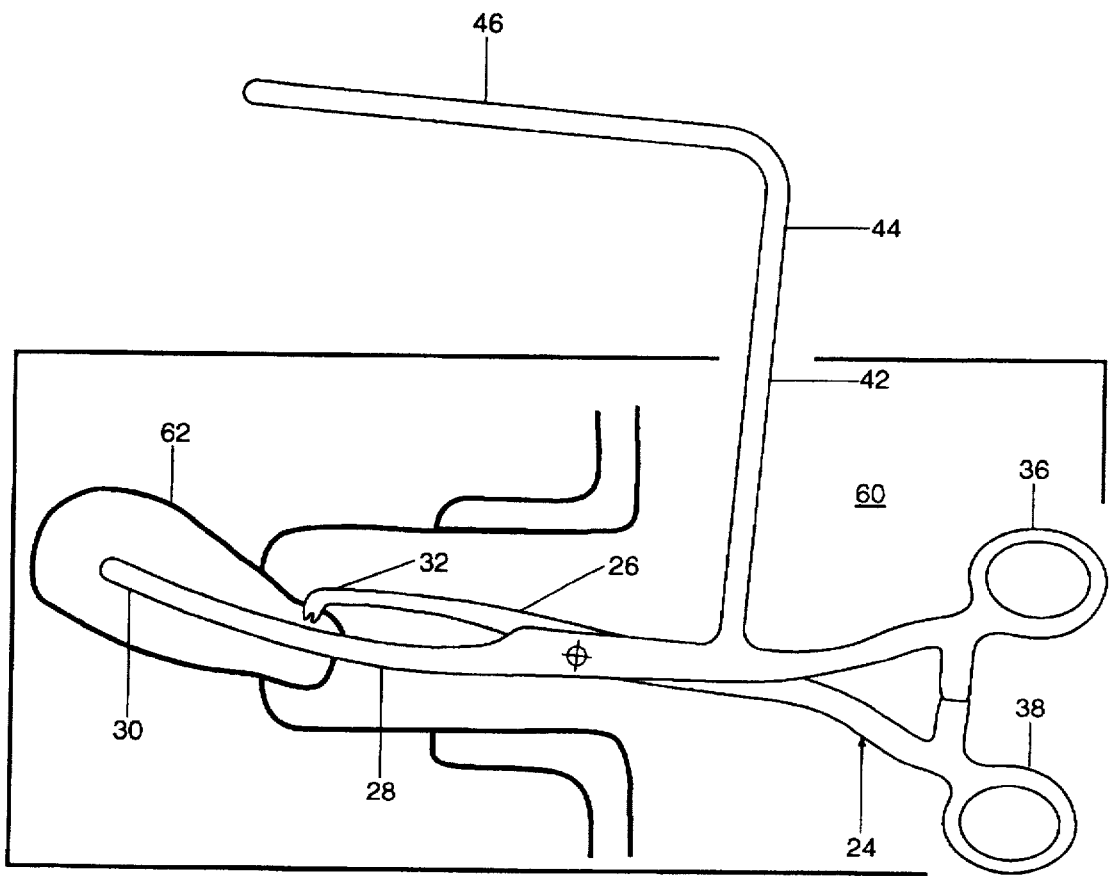
FIG. 3 shows a surgical instrument of the present invention affixed to the uterus of a patient.

Referring now to FIG. 3, clamp 24 is shown in use with the ends 32 and 30 of arms 26 and 28 clamped to uterus 62. Grip 44 is shown integrally formed with arm 28. Member 42 of grip 44 extends perpendicularly from arm 28 and is of sufficient length to clear the sterile operation field 60 such that member 46 of grip 44 is outside of the sterile operation field 60 with clamp 24 affixed to uterus 62. Accordingly, clamp 24 can be engaged to maneuver the uterus from above the sterile operation field.

Figure 1:
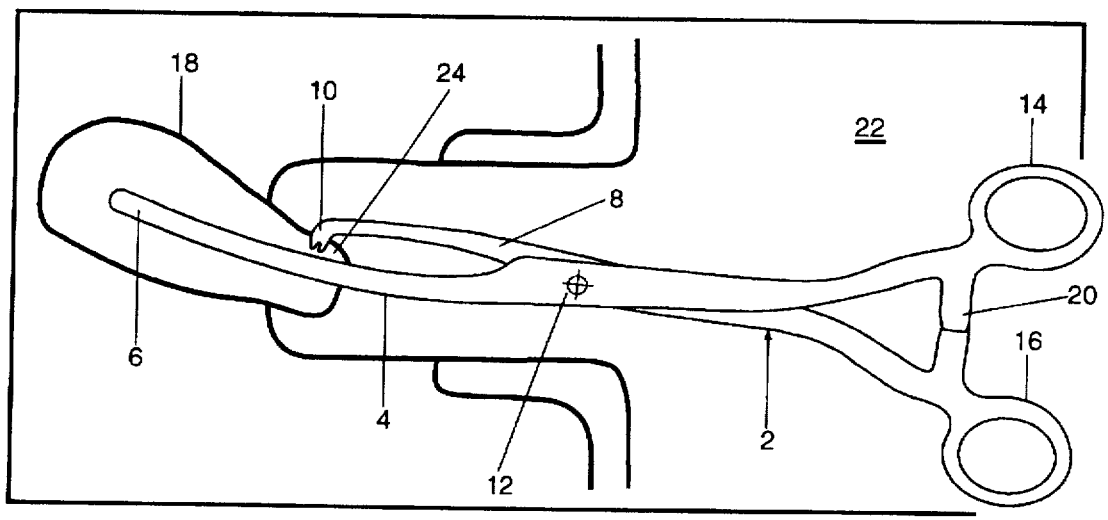
FIG. 1 diagrammatically shows a prior art uterine clamp affixed to the uterus of a patient.

Several of the advantages of clamp 24 over the prior art clamp 2 (FIG. 1) can be gleaned most clearly from FIGS. 7(a) and 7(b). In FIG. 7(a), prior art clamp 2 is shown clamped to the uterus of a patient. The patient is covered by a sterile clinical drape 84 which separates non-aseptic area 88 from sterile (aseptic) area 86. It can readily be appreciated that manipulation of clamp 2 requires a presence within area 86. By contrast, as shown in FIG. 7(b), member 42 of grip 44 extends through clinical drape 90 such that member 46 of grip 44 can be engaged to maneuver the uterus of the patient from non-aseptic area 94, i.e. outside of sterile area 92. Moreover, since grip member 46 extends from grip member 42 in a direction toward the uterus to which the clamp is affixed, it can be maneuvered by an assistant facing in the same direction as the patient to be treated. Since the directional orientation of such an assistant will be the same as the directional orientation of the patient, communication between the operating surgeon and the assistant will be improved. Moreover, grip 44 provides for simplified mobilization of the uterus and thus frees the assistant to aid the operating physician in other ways. Additionally, the assistant is no longer in proximity to the surgeon and interference between them is eliminated. Alternatively, grip 44 allows the surgeon himself to mobilize the uterus in the desired position.

Figure 5:
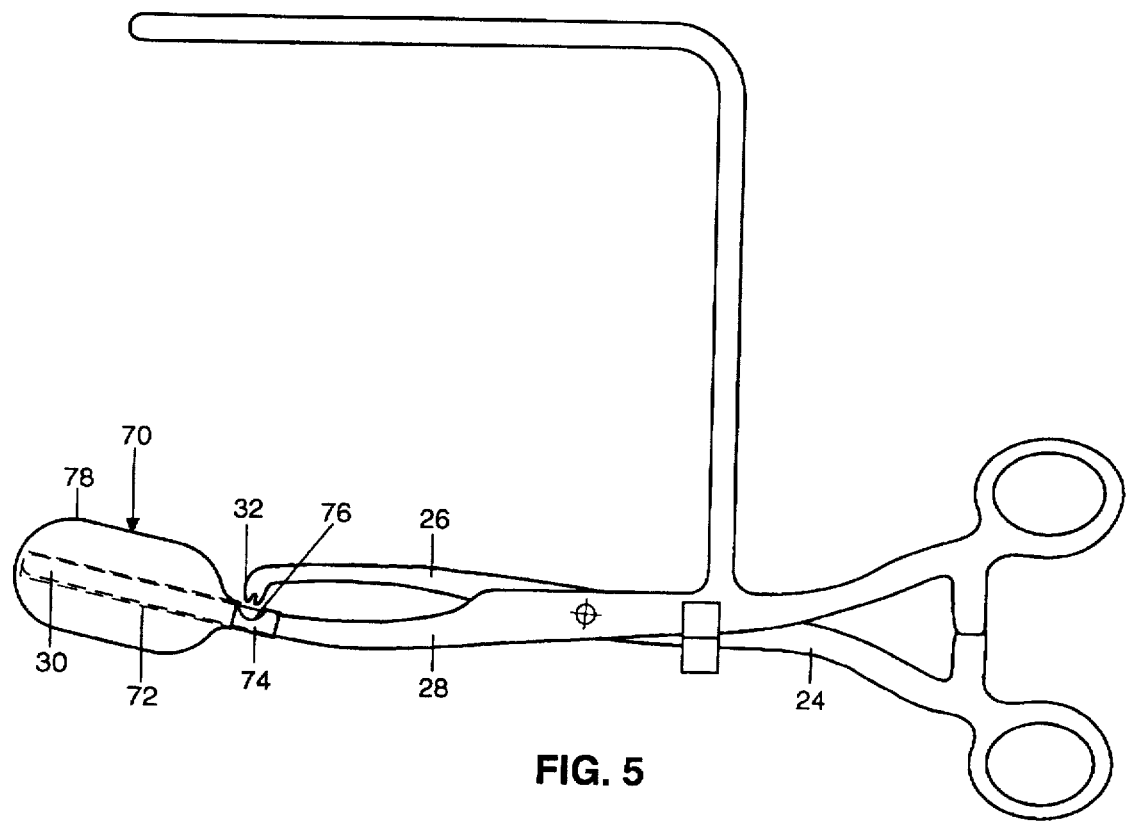
FIG. 5 shows a cylindrical shaped attachment on an end of the surgical instrument of the invention.

An attachment to the present clamp makes it possible to use the clamp in cases where the patient has had a hysterectomy and manipulation/elevation of the vagina and bladder is desired. FIG. 5 shows an attachment 70 of cylindrical shape that is detachably affixed to end 30 of arm 28 of uterine clamp 24 of the invention. The attachment 70 has an external housing 78 which provides the attachment with its cylindrical shape. Attachment 70 has a sleeve 72 extending through the entire length of housing 78. The sleeve 72 is preferably tubular in shape and dimensioned to accommodate end 30 of long arm 28 of clamp 24 in tight fitting relation. Accordingly, the sleeve will preferably have a diameter "v" (FIG. 4) that corresponds to the diameter of the long arm 28 of the clamp. Sleeve 72 is provided with collar 74 to facilitate fastening the attachment to the long arm 28 of the clamp (see FIG. 5). Collar 74 is provided with a recessed wall portion 76 which allows the arm 28 to be exposed at a position along the arm at which the end 32 of the short arm 26 of the clamp makes contact when the clamp is in a clamping position (see FIG. 5).

Figure 4:
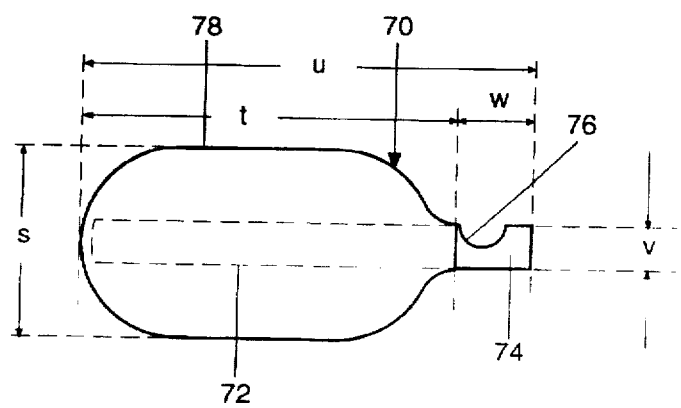
FIG. 4 shows a cylindrical shaped attachment of the present invention.

The dimensions of the housing 78 of attachment 70 should approximate the dimensions of a woman's vagina. Referring to FIG. 4, in a typical embodiment, a preferred dimension for the width ("s") of housing 78 is about 30 mm. A preferred dimension for the length ("t") of housing 78 is about 55 mm. A preferred dimension for the collar 74 is about 15 mm. Accordingly, the overall length ("u") of attachment 70 in a typical embodiment will be about 70 mm.

Figure 6:
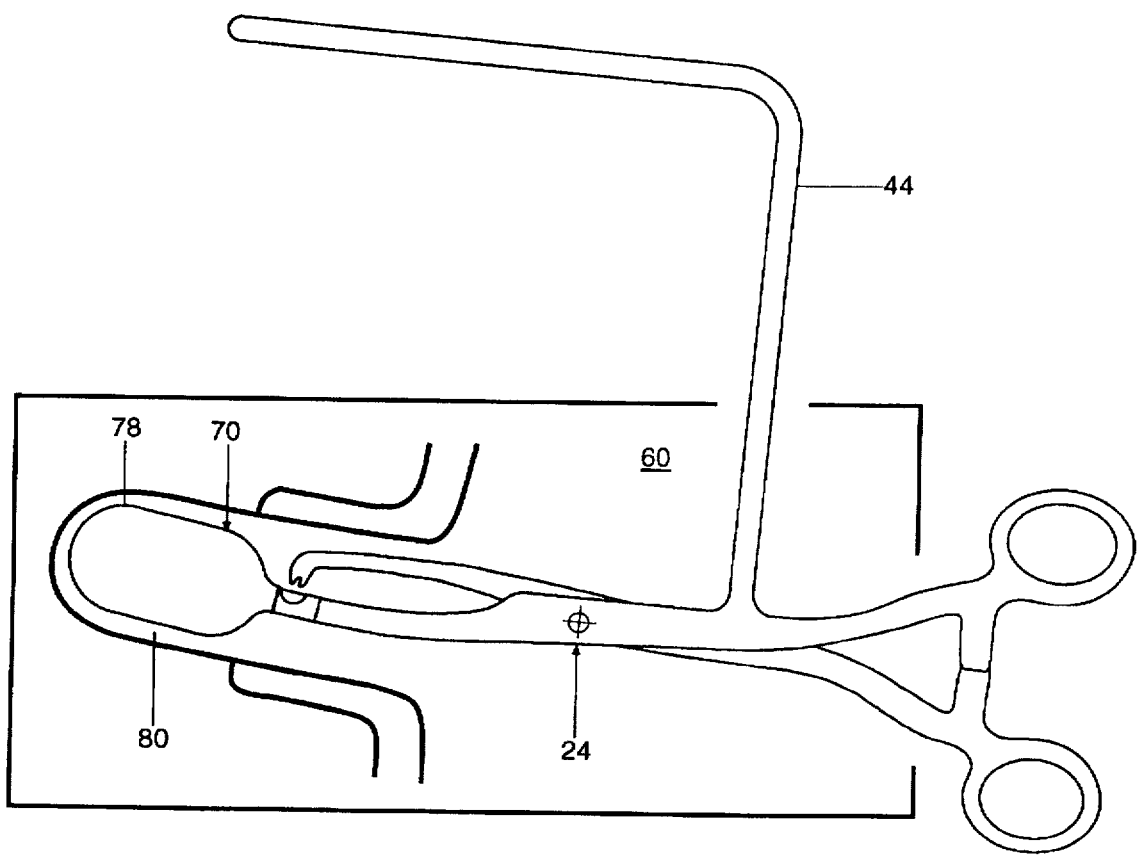
FIG. 6 shows the surgical instrument with the cylindrical-shaped attachment within a sterile operating area.

FIG. 6 shows clamp 24 of the invention with cylindrical shaped attachment 70 positioned within a vaginal cavity 80 from which a uterus has been removed. It will be appreciated that the use of this attachment enables the manipulation of the vagina and bladder of a patient through the use of grip 44 by an assistant outside of the sterile operating area 60.

While this invention has been described and illustrated with respect to a preferred embodiment of the invention, it will be apparent that many changes and modifications may be made in the general construction and arrangement of the present invention without departing from the spirit and scope thereof. Therefore, it is desired that the invention be limited not to the exact disclosure but only to the extent of the appended claims and equivalents.

I claim:

1. A surgical instrument for fixation and elevation of an internal body part of a patient, wherein the internal body part is present within a sterile operating area, comprising first and second pivotably connected arms having ends which can be moved towards and away from one another when the arms are pivotably moved, clamp means on the ends of the arms for engaging the internal body part of the patient to manipulate and elevate the body part, and projecting guide member means, having a first end fixed on one of said arms, a second end that is free and unattached and a manually engagable portion remote from the arms, for manipulating said arms remotely therefrom to enable manipulation and elevation of said body part from an area remote from the sterile operating area.

2. A surgical instrument as claimed in claim 1 wherein said arms have opposite ends remote from said ends with the clamp means and finger-engaging portions at said opposite ends, said guide member includes a portion extending perpendicularly from said arm to which the first end is fixed, said manually engagable portion extending from said perpendicularly-extending portion in a direction away from said finger-engaging portions.

3. A surgical instrument as claimed in claim 2 where said guide member is of L-shape.

4. A surgical instrument as claimed in claim 3 wherein said arms are connected in scissor fashion, said guide member extending from said arms in the vicinity of the pivotable connection of said arms.

5. A surgical instrument as claimed in claim 4 wherein said manually engagable portion extends approximately parallel to said arms when the arms are closed.

6. A surgical instrument as claimed in claim 5 wherein said manually engagable portion of the guide member is dimensioned relative to said arms to produce substantially 1:1 movement of said clamp means and said manually engagable member in the same direction.

7. A surgical instrument as claimed in claim 6 wherein for patients lacking a uterus, said instrument further comprises an additional element attachable to one of said arms and of cylindrical shape.

8. A surgical instrument as claimed in claim 5 wherein the body part of the patient to be manipulated is the uterus, said clamp means being shaped to engage and clamp the uterus.

9. A surgical instrument as claimed in claim 5 wherein the manually engagable portion has a length that is greater than a distance from the pivotal connection of said arms to said clamp means.

10. A surgical instrument as claimed in claim 9 wherein the length of the manually engagable portion is about 160 mm.

11. A surgical instrument as claimed in claim 2 wherein the perpendicularly-extending member has a length that is greater than a distance from the pivotal connection of said arms to said clamp means.

12. A surgical instrument as claimed in claim 11 wherein the length of the perpendicularly extending member is about 260 mm.

13. A surgical instrument as claimed in claim 1 comprising hook means for guiding a catheter into a second body part of the patient when the clamp means is engaging the internal body part.

14. A surgical instrument as claimed in claim 13 wherein the hook means is positioned in the vicinity of the pivotable connection of the arms and is of J-shape in profile.

15. A surgical instrument as claimed in claim 14 wherein the second body part is a bladder.

16. A surgical instrument as claimed in claim 1 wherein said instrument further comprises uterine-shaped means attachable to one of said arms for manipulation of the vagina and bladder of a female patient lacking a uterus.

* * * * *